United States Patent [19]

Melcher et al.

[11] Patent Number: 5,064,009
[45] Date of Patent: Nov. 12, 1991

[54] DEVICE FOR THE DETERMINATION OF DRY SUBSTANCE

[75] Inventors: Franz-Josef Melcher, Hardegsen; Thomas Pertsch, Göttingen; Wilfried Spannagel, Göttingen; Christian Oldendorf, Göttingen, all of Fed. Rep. of Germany

[73] Assignee: Sartorius AG, Göttingen, Fed. Rep. of Germany

[21] Appl. No.: 558,461

[22] Filed: Jul. 27, 1990

[51] Int. Cl.$^5$ ............................................. G01G 19/00
[52] U.S. Cl. .................................. 177/245; 177/145; 177/54; 364/568
[58] Field of Search ................. 177/145, 245, 146, 54; 364/568

[56] References Cited

U.S. PATENT DOCUMENTS

| 2,515,412 | 7/1950 | Lee | 177/145 |
| 4,562,044 | 12/1985 | Bohl | 177/145 X |
| 4,849,175 | 7/1989 | Dupain et al. | 177/54 X |

Primary Examiner—George H. Miller, Jr.
Attorney, Agent, or Firm—Eric P. Schellin

[57] ABSTRACT

A device for the determination of dry substance of specimens consists of a microwave heater (10) and of a balance (5) whose balance scale (4) is located within the microwave heating area (7). This device includes a rotary disk (1) located within the microwave heating area (7) which disk can receive several specimen containers (2) and by elevating means which can raise and lower one of the specimen containers (2) from the rotary disk (1) and place it on the balance scale (4). The elevating means consists e.g. of a lifting device (11) for the rotary disk (1).

9 Claims, 2 Drawing Sheets

5,064,009

DEVICE FOR THE DETERMINATION OF DRY SUBSTANCE

BACKGROUND OF THE INVENTION

The invention relates to a device for the determination of dry substance of specimens with microwave heating and with a balance. The balance scale is located within the microwave heating area.

Devices of this type for the determination of dry substance are known e.g. from U.S. Pat. No. 3,909,598 or Japanese patent 51-136-489.

The use of microwave heating has the advantages over infrared radiant heating and direct heating in that a uniform heating of the specimens takes place and that only a relatively slight excess temperature is achieved during the drying process. The lower drying temperature prevents to a large extent a physical and chemical change of the specimens. Volatile substances which volatize at higher temperatures in addition to the water from the specimen and falsify the measured moisture value remain in the material at rather low temperatures. Moreover, the drying speed is greater for many specimens than in traditional heating methods.

However, the known devices for the determination of dry substance with microwave heating have the disadvantage that considerable design expenses are necessary in order to maintain the field strength of the microwave heating so constant over the entire surface of the specimen that a uniform drying is achieved.

The invention has the object of detailing a device for the determination of dry substance which permits a more uniform drying of the specimen and also further increases the number of specimens which can be measured during a certain period of time.

SUMMARY OF THE INVENTION

The invention solves this problem in that a rotary disk is additionally located inside the microwave heating area which disk can receive several specimen dishes and in that auxiliary means are present which can raise one of these specimen dishes at a time from the rotary disk and place it on the balance scale.

The invention therefore makes use of the rotary plate principle known in microwave baking devices for achieving a uniform drying and expands this principle by means of the arrangement of several specimens on the rotary plate. As a result, several specimens can be dried at the same time. As a result of using the auxiliary means, which can raise the specimen dishes one at a time from the rotary disk and place it on the balance scale, the device for the determination of dry substance can nevertheless make do with one balance, so that the expense is hardly increased by the design of the present invention.

BRIEF DESCRIPTION OF THE DRAWINGS

The invention is described in the following with reference made to the schematic Figures.

DETAILED DESCRIPTION OF THE DRAWINGS

Figure 1:
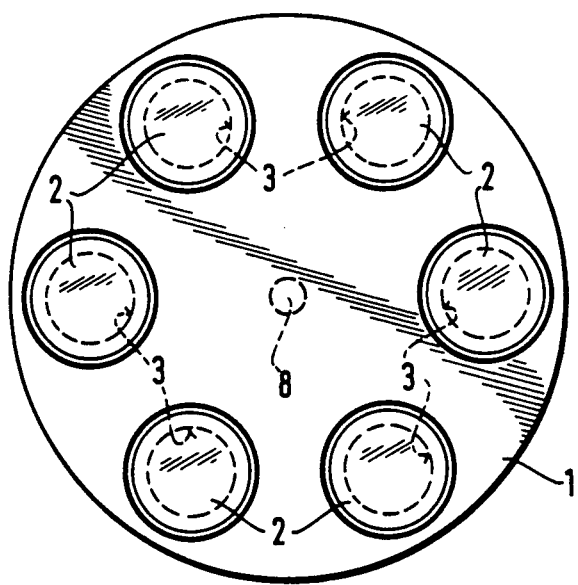
FIG. 1 shows a top view of the rotary disk.
Figure 2:
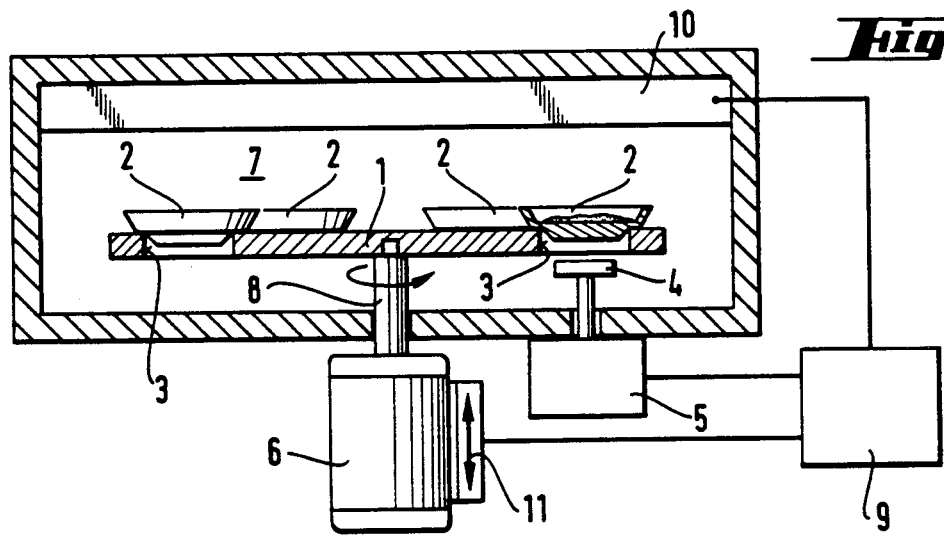
FIG. 2 shows a section through the rotary disk with lifting device and balance in rotary position.
Figure 3:
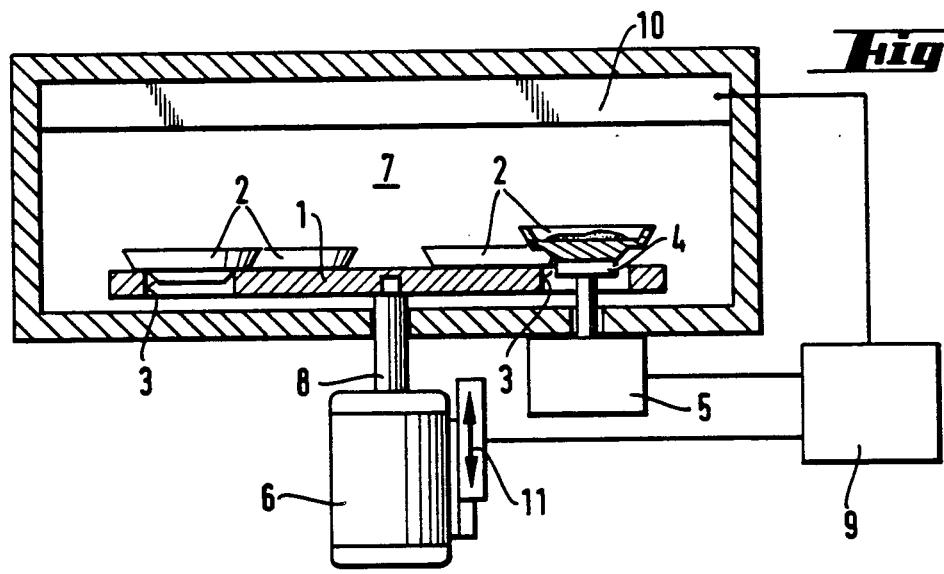
FIG. 3 shows a section through the rotary disk with lifting device and balance in weighing position.

A first embodiment of the device for the determination of dry substance is shown in FIGS. 1 to 3. In FIG. 1 it is shown as a top view of the rotary disk 1 and in FIGS. 2,3 as a section through the microwave heater area 7 the rotary disk with a lifting device 11, plus balance 5 and microwave heating device 10. In FIG. 2 in rotary position. In FIG. 3 in weighing position. Rotary disk 1 comprises several openings 3 arranged at equal intervals to axle of rotation 8. A specimen disk 2 can be inserted into each opening 3 in such a manner that it is centered by opening 3. Rotary disk 1 is detailed to be driven in slow rotation by means of motor 6. The rotary motion of rotary disk 1 can be stopped by control and evaluation unit 9 in such a manner that one of openings 3 remains positioned exactly over load receiver 4 of balance 5. If the lifting device, which is indicated only by double arrow 11, is actuated in this position, thus lowering the entire rotary disk 1, one of specimen dishes 2 is placed on load receiver 4 of balance 5 for weighing (position of FIG. 3). After the termination of the weight; lifting device 11 raises rotary disk 1 again, specimen dish 2 is lifted off of load receiver 4 of balance 5 and rests again in its associated opening 3 of rotary disk 1. Rotary disk 1 can execute for example several complete revolutions in this position shown in FIG. 2 in order to move the various specimens 2 into the field ranges of the microwave heating zone (schematically indicated with 10), which can achieve differing power as desired, thus achieving a uniform drying of all specimens. Rotary disk 1 then stops in such a manner that another specimen 2 is located exactly over load receiver 4 of balance 5 and can be placed thereon for weighing the manner heretofore described.

Control and evaluating unit 9 assures the stopping of rotary disk 1 in the correct position (for this, a stepping motor can be used as motor 6, or control and evaluating unit 9 can obtain the information via the position of rotary disk 1 by means of contact makers as sensors) for the actuation of lifting device 11, for setting specimen dish 2 onto load receiver 4 of balance 5, for raising rotary disk 1 again after termination of the weighing and for the selection of the next specimen for the weighing process. Depending on the requirements of the specimen substances, the weighing can either be performed as frequently as possible or time periods can be inserted between the individual measurements on which time periods the rotary disk only rotates and no weighing takes place. Since a weighing requires only approximately 2 seconds, a complete weighing and specimen-replacement process lasts only approximately 5 seconds before the next adjacent specimen is weighed As the example discussed is of 6 specimens, these six specimens can all be measured once in approximately 30 seconds.

Furthermore, control and evaluating unit 9 associates the measured weight values with the particular specimens and stores them under the specimen number. This also includes the fact that control and evaluating unit 9 determines the tare values of the individual specimen dishes 2 in an empty passage; stores them and considers them in the determination of the dry-substance content. Moreover, control and evaluating device 9 controls microwave heating 10. In the simplest case, this signifies the cutting in of the microwave heating as soon as the starting weight of all specimens has been determined and the cutting out of the microwave heating as soon as all specimens exhibit a weight loss per time unit which loss is at least below a set limit value. In addition, in a preferred embodiment the performance of microwave heating 10 is regulated as a function of the course of the weight-loss curves in such a manner that at the start of the drying steps a maximum drying speed is achieved and toward the end of the drying, however, too strong a heating of the specimen is avoided.

Moreover, the control and evaluating unit is designed to calculate an extrapolation from the measured weight-loss curve, as is known from U.S. Pat. No. 4,889,207 thus outputting an estimated value for the dry-substance content before the drying has been completely concluded. This can shorten the required measuring time even further.

If identical substances are located in the various specimen dishes, control and evaluating unit 9 can advantageously determine the average value and the standard deviation of the dry-substance contents of all specimens after the conclusion of the drying, therewith making possible a statistical support for the measured value.

Control and evaluating unit 9 is advantageously achieved by a microprocessor in order to fulfill all these control, storage and calculating tasks.

Figure 4:
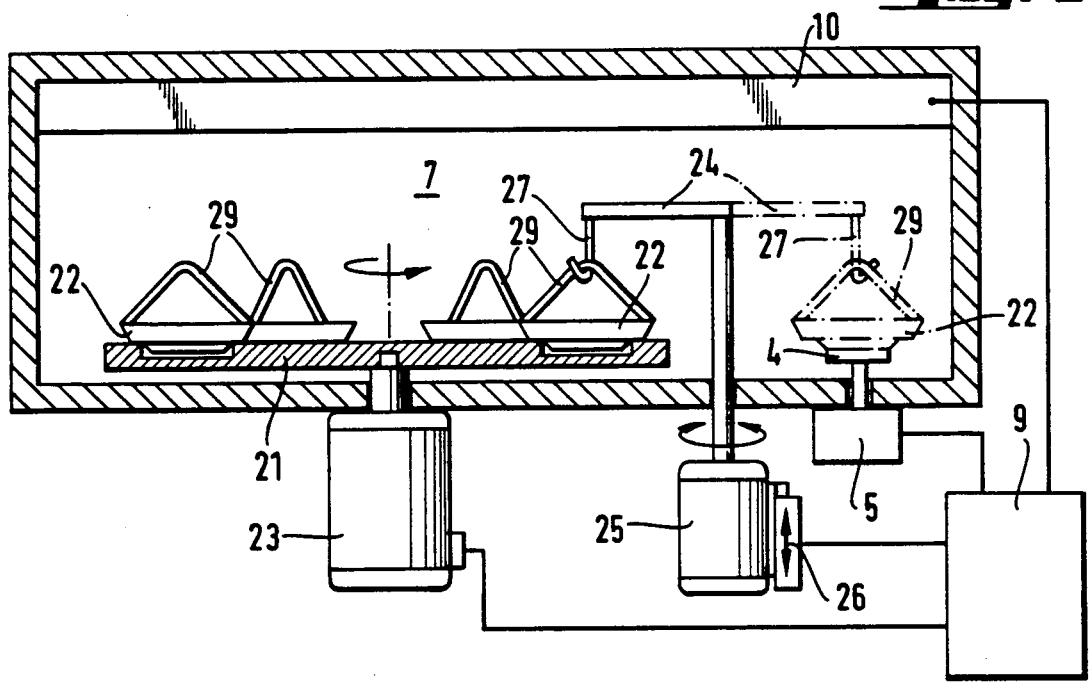
FIG. 4 shows a section through the rotary disk with pivotable bracket and balance as the second embodiment of the device.

FIG. 4 shows a second embodiment in section with rotary risk, bracket, balance and microwave heating. Rotary disk 21 is rotated by a motor 23; however, a vertical movement of rotary disk 21 is not provided. A bracket 24 is provided to raise specimen dishes 22 from rotary disk 21.

This bracket 24 can be raised by a lifting device which is indicated only by double arrow 26, whereby hook 27 reaches under handle 29 on specimen dish 22 and raises the latter. Then, bracket 24 is pivoted by motor 25 through 180° and then lowered again, whereby specimen dish 22 is placed on load receiver 4 of balance 5. After the weighing, the return transport of specimen dish 22 onto rotary disk 21 takes place in a corresponding manner. Rotary disk 21, bracket 24 and load receiver 4 of balance 5 are also located in heating area 7 of a microwave heater 10. The control likewise takes place in the same manner as in the first embodiment by means of a control and evaluating unit 9. This second embodiment has the advantage that rotary disk 21 can execute e.g. a further revolution during the weighing step, so that an even better data about any inhomogeneities of the microwave field takes place, which renders the heating of the specimens even more uniform.

Figure 5:
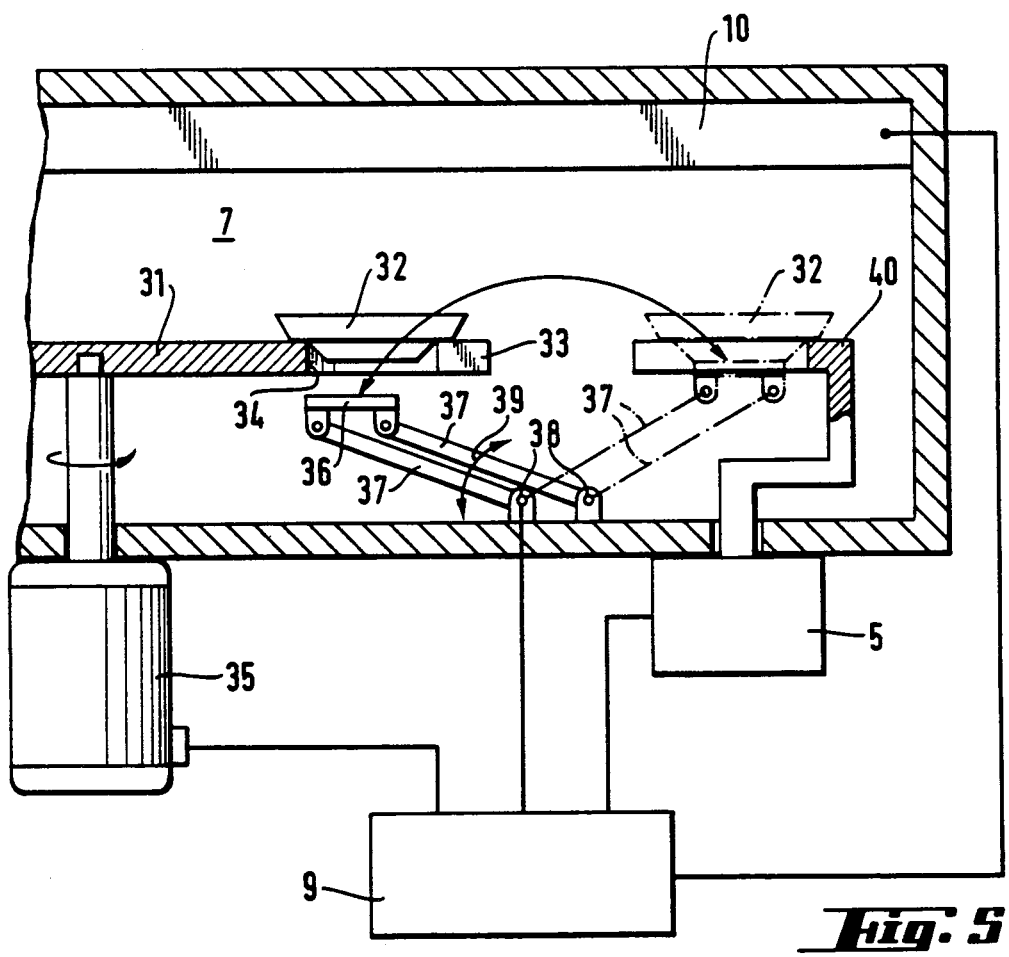
FIG. 5 shows a section through the rotary disk with pivoting device and balance as the third embodiment of the device.

FIG. 5 shows a third embodiment in section with rotary disk, circular-arc pivoter, balance and microwave heater. Rotary disk 31 comprises radial slots 33 in this embodiment which are widened in a circular fashion at their ends 34 and form a bearing for specimen dishes 32. Rotary disk 32 can be rotated by motor 35. A circular-arc pivoter is provided for raising specimen dish 32, which pivoter consists of carrier plate 36 connected by two struts 37 in a movable fashion to points 38 fixed to the housing. When struts 37 are pivoted, carrier plate 36 moves in a circular arc but maintains its horizontal position. Specimen dish 32 can be raised from rotary disk 31 by this circular-arc pivoter and placed onto load receiver 40 of balance 5 again, which is likewise provided with a slot. The drive for this circular-arc pivoter is indicated only by double arrow 39 and is likewise controlled by control and evaluating unit 9. This third embodiment had the advantage over the second embodiment that the lifting and rotary motion is combined to a rotary motion.

The lifting and rotating drives, the balance and the microwave heater are indicated and described only in a schematic manner above since the design and the operation of all these components are generally known.

What is claimed is:

1. A device for the determination of dry substance of specimens with a microwave heater (10) and with a balance (5) whose balance scale (4,40) is located within the microwave heater area (7), comprising a rotary disk (1,21,31) located inside the microwave heater area (7) which disk is adapted and constructed to carry a plurality of specimen dishes (2,22,32), elevating means to raise sequentially one of said specimen dishes (2,22,32) from the rotary disk and position it on the balance scale (4,40).

2. The device for the determination of dry substance according to claim 1, wherein the elevating means consists of a lifting device (11) for the rotary disk (1).

3. The device for the determination of dry substance according to claim 1, wherein the elevating means consists of a bracket (24) adapted and constructed to execute both a vertical and a pivoting motion.

4. The device for the determination of dry substance according to claim 1, wherein the elevating means consists of a circular-arc pivoter means.

5. The device for the determination of dry substance according to claim 1, wherein a control and evaluating unit means (9) is present which controls the rotary motion of the rotary disk (1,21,31) and the elevating means adapted and constructed to raise sequentially one of the specimen dishes from rotary disk and place it onto the said balance scale (4,40) and stores the weight values measured by the balance (5) and associates them with the individual specimens.

6. The device for the determination of dry substance according to claim 5, wherein the control and evaluating unit means (9) regulates the performance of the microwave heating (10) as a function of the course of the weight-loss curves.

7. The device for the determination of dry substance according to claim 6, wherein the control and evaluating unit means (9) is adapted and constructed to determine the end of drying from the course of the weight-loss curves.

8. The device for the determination of dry substance according to claim 7, wherein the control and evaluating unit means (9) is adapted and constructed to determine the average value and the standard deviation of the dry-substance contents of all specimens on the rotary disk (1,21,31).

9. The device for the determination of dry substance according to claim 8, wherein the control and evaluating unit means (9) is a microprocessor.

* * * * *